US00PP19168P2

(12) United States Plant Patent
Smith

(10) Patent No.: US PP19,168 P2
(45) Date of Patent: Sep. 2, 2008

(54) ***CHRYSANTHEMUM* PLANT NAMED 'WARM YOIGLOO'**

(50) Latin Name: *Chrysanthemum×morifolium*
Varietal Denomination: Warm Yoigloo

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/705,880

(22) Filed: Feb. 14, 2007

(51) Int. Cl.
*A01H 5/00* (2006.01)

(52) U.S. Cl. ..... Plt./296

(58) Field of Classification Search ..... Plt./296, Plt./290

See application file for complete search history.

*Primary Examiner*—Kent L. Bell
*Assistant Examiner*—June Hwu
(74) *Attorney, Agent, or Firm*—C. A. Whealy

(57) ABSTRACT

A new and distinct cultivar of *Chrysanthemum* plant named 'Warm Yoigloo', characterized by its upright, outwardly spreading and mounding plant habit; freely branching habit; dense and full plant habit; uniform and freely flowering habit; duplex-type inflorescences with obovate-shaped ray florets; orange bronze-colored ray florets; and natural season flowering about September 17$^{th}$ in the Northern Hemisphere.

1 Drawing Sheet

Botanical designation: *Chrysanthemum×morifolium.*
Cultivar denomination: 'WARM YOIGLOO'.

BACKGROUND OF THE INVENTION

The present invention relates to a new and distinct cultivar of *Chrysanthemum* plant, botanically known as *Chrysanthemum×morifolium,* commercially grown as a perennial garden *Chrysanthemum* and hereinafter referred to by the name 'Warm Yoigloo'.

The objective of the breeding program is to create new perennial garden-type *Chrysanthemum* cultivars having inflorescences with desirable inflorescence forms, attractive florets colors and good garden performance.

The new *Chrysanthemum* originated from a cross-pollination made by the Inventor in December, 2000, in Salinas, Calif. of a proprietary seedling selection of *Chrysanthemum×morifolium* identified as code number 95-L464005, not patented, as the female, or seed, parent with the *Chrysanthemum×morifolium* cultivar Mei Kyo, not patented, as the male, or pollen, parent. The new *Chrysanthemum* was discovered and selected by the Inventor as a single flowering plant within the progeny of the stated cross-pollination in a controlled environment in Alva, Fla. in October, 2001. The selection of this plant was based on its desirable inflorescence color and good form and substance.

Asexual reproduction of the new *Chrysanthemum* by vegetative cuttings was first conducted in Alva, Fla. in January, 2002. Asexual reproduction by cuttings has shown that the unique features of this new *Chrysanthemum* are stable and reproduced true to type in successive generations.

SUMMARY OF THE INVENTION

Plants of the cultivar Warm Yoigloo have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Warm Yoigloo'. These characteristics in combination distinguish 'Warm Yoigloo' as a new and distinct garden *Chrysanthemum* cultivar:

1. Upright, outwardly spreading and mounding plant habit.
2. Freely branching habit; dense and full plant habit.
3. Uniform and freely flowering habit.
4. Duplex-type inflorescences with obovate-shaped ray florets.
5. Orange bronze-colored ray florets.
6. Natural season flowering about September 17$^{th}$ in the Northern Hemisphere.

In side-by-side comparisons conducted in Alva, Fla., plants of the new *Chrysanthemum* differed from plants of the female parent selection, in the following characteristics:

1. Plants of the new *Chrysanthemum* flowered 10 to 14 days later than plants of the female parent selection when grown under natural season conditions.
2. Plants of the new *Chrysanthemum* and the female parent selection differed in ray floret color as plants of the female parent selection had white-colored ray florets.
3. Plants of the new *Chrysanthemum* had more disc florets than plants of the female parent selection.

In side-by-side comparisons conducted in Alva, Fla., plants of the new *Chrysanthemum* differed from plants of the male parent, the cultivar Mei Kyo, in the following characteristics:

1. Plants of the new *Chrysanthemum* were smaller than plants of the cultivar Mei Kyo.
2. Plants of the new *Chrysanthemum* flowered about one month earlier than plants of the cultivar Mei Kyo when grown under natural season conditions.
3. Plants of the new *Chrysanthemum* had larger inflorescences than plants of the cultivar Mei Kyo.
4. Plants of the new *Chrysanthemum* and the cultivar Mei Kyo differed in ray floret color as plants of the cultivar Mei Kyo had pale lavender-colored ray florets.

Plants of the new *Chrysanthemum* can be compared to plants of the *Chrysanthemum* cultivar MN95-105-6, disclosed in U.S. Plant Pat. No. 14,129. In side-by-side comparisons conducted in Alva, Fla., plants of the new *Chrysanthemum* differed from plants of the cultivar MN95-105-6 in the following characteristics:

1. Plants of the new *Chrysanthemum* were fuller and more mounded than plants of the cultivar MN95-105-6.
2. Plants of the new *Chrysanthemum* had smaller inflorescences with more ray florets than plants of the cultivar MN95-105-6.
3. Plants of the new *Chrysanthemum* and the cultivar MN95-105-6 differed in ray floret color as plants of the cultivar MN95-105-6 had coral pink-colored ray florets.
4. Ray floret color of plants of the new *Chrysanthemum* did not fade as quickly as ray floret color of plants of the cultivar MN95-105-6.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of a typical flowering plant of 'Warm Yoigloo'.

The photograph at the top of the sheet is a close-up view of typical inflorescences of 'Warm Yoigloo'.

DETAILED BOTANICAL DESCRIPTION

The aforementioned photographs and following observations and measurements describe plants grown in Pendleton, S.C. during the summer in an outdoor nursery and under conditions and practices which approximate those generally used in commercial garden *Chrysanthemum* production. During the production of the plants, day temperatures averaged 32° C. and night temperatures averaged 21° C. Plants were grown in 20 cm-containers under natural season conditions. Plants used in the photographs and for the description were about four months old. In the following description, color references are made to The Royal Horticultural Society Colour Chart, 1995 Edition, except where general terms or ordinary dictionary significance are used.

Botanical classification: *Chrysanthemum×morifolium* cultivar Warm Yoigloo.

Parentage:

*Female, or seed, parent.*—Proprietary seedling selection of *Chrysanthemum×morifolium* identified as code number 95-L464005, not patented.

*Male, or pollen, parent.*—*Chrysanthemum×morifolium* cultivar Mei Kyo, not patented.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Perennial duplex-type garden *Chrysanthemum*. Stems upright and outwardly spreading giving a uniformly mounded appearance to the plant. Freely branching habit, about ten lateral branches each with multiple secondary and tertiary branches; pinching is not required; dense and full plant habit. Strong and vigorous growth habit.

*Plant height.*—About 28 cm.

*Plant width.*—About 59 cm.

*Lateral branches.*—Length: About 28 cm. Diameter: About 8 mm. Internode length: About 1.5 cm to 2.8 cm. Strength: Strong. Texture: Pubescent. Color: 148A.

*Leaves.*—Arrangement: Alternate, simple. Length: About 4.2 cm. Width: About 2.8 cm. Apex: Cuspidate to mucronate. Base: Attenuate. Margin: Palmately lobed, sinuses between lateral lobes parallel to convergent. Texture, upper and lower surfaces: Pubescence; veins prominent on lower surface. Color: Developing and fully expanded foliage, upper surface: 137A; venation, 138A. Developing and fully expanded foliage, lower surface: 137C; venation, 138A. Petiole: Length: About 8 mm. Diameter: About 3 mm. Texture, upper and lower surfaces: Pubescent. Color, upper and lower surfaces: 147B.

Inflorescence description:

*Appearance.*—Duplex-type inflorescence form with obovate-shaped ray florets. Inflorescences borne on terminals above foliage. Disk and ray florets arranged acropetally on a capitulum. Inflorescences fragrant, typical of *Chrysanthemum*.

*Flowering response.*—Under natural season conditions, plants flower about September 17$^{th}$ in the Northern Hemisphere.

*Postproduction longevity.*—Inflorescences maintain good color and substance for about four weeks in an outdoor nursery. Inflorescences persistent.

*Quantity of inflorescences.*—About 103 inflorescences develop per lateral branch.

*Inflorescence bud.*—Height: About 1.1 cm. Diameter: About 1.4 cm. Shape: Oblate. Color: 171D.

*Inflorescence size.*—Diameter: About 4 cm. Depth (height): About 1.7 cm. Disc diameter: About 6 mm. Receptacle height: About 5 mm. Receptacle diameter: About 1.8 cm.

*Ray florets.*—Shape: Obovate. Orientation: Initially upright, then about 90° from vertical; eventually reflexing. Aspect: Initially incurved, then mostly flat. Length: About 1.8 cm. Width: About 4 mm. Apex: Emarginate. Base: Acute. Margin: Entire. Texture, upper and lower surfaces: Smooth, glabrous; longitudinally ribbed. Number of ray florets per inflorescence: About 320 arranged in about 19 to 21 whorls. Color: When opening, upper surface: 173B. When opening, lower surface: 173D. Fully opened, upper surface: Outer ray florets, 172D, color becoming closer to 168D with development; inner ray florets, 173B, towards the apex, 167D. Fully opened, lower surface: 173D.

*Disc florets.*—Shape: Tubular, elongated. Length: About 3 mm. Diameter: Less than 1 mm. Number of disc florets per inflorescence: About 154. Color, immature and mature: Apex: Close to 12A. Midsection: Close to 12D. Base: Close to 1D.

*Phyllaries.*—Number of phyllaries per inflorescence: About 30 arranged in about five whorls. Length:

About 7 mm. Width: About 3 mm. Shape: Elliptical. Apex: Acute. Base: Truncate. Texture, upper surface: Smooth, glabrous. Texture, lower surface: Pubescent. Color, upper surface: Close to 144A. Color, lower surface: Close to 146B.

*Peduncles.*—Length: About 5.8 cm. Diameter: About 1 mm. Angle: Mostly upright or curving upright. Strength: Strong. Texture: Pubescent. Color: Close to 194A.

*Reproductive organs.*—Androecium: None observed on disc florets. Gynoecium: Present on both ray and disc florets. Pistil length: About 5 mm. Stigma shape: Bi-parted. Stigma color: Close to 7A. Style length: About 3 mm. Style color: Close to 8B. Ovary color: Close to 157A.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and will overwinter in USDA Zones 5 and higher; plants of the new *Chrysanthemum* have been observed to tolerate high temperature of about 38° C.

It is claimed:

1. A new and distinct *Chrysanthemum* plant named 'Warm Yoigloo' as illustrated and described.

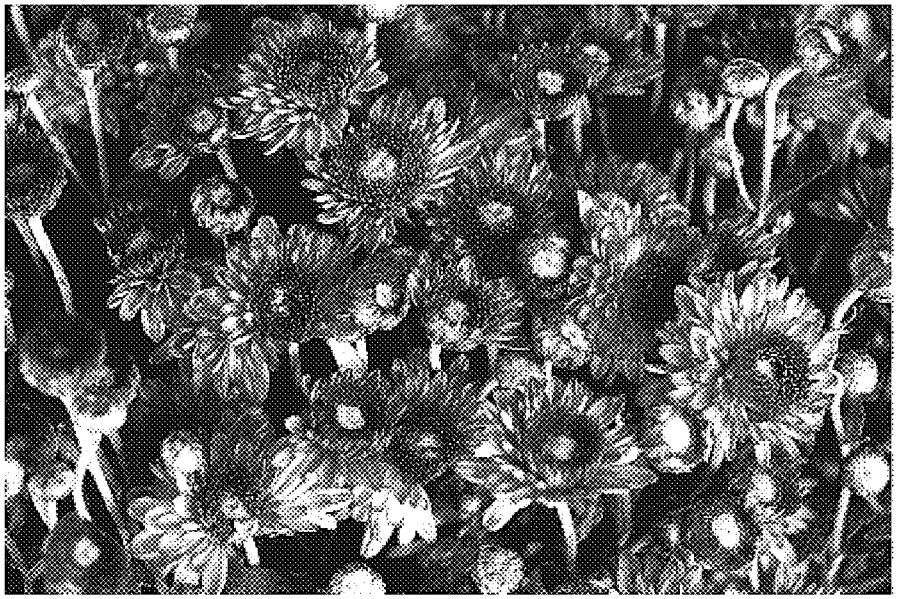
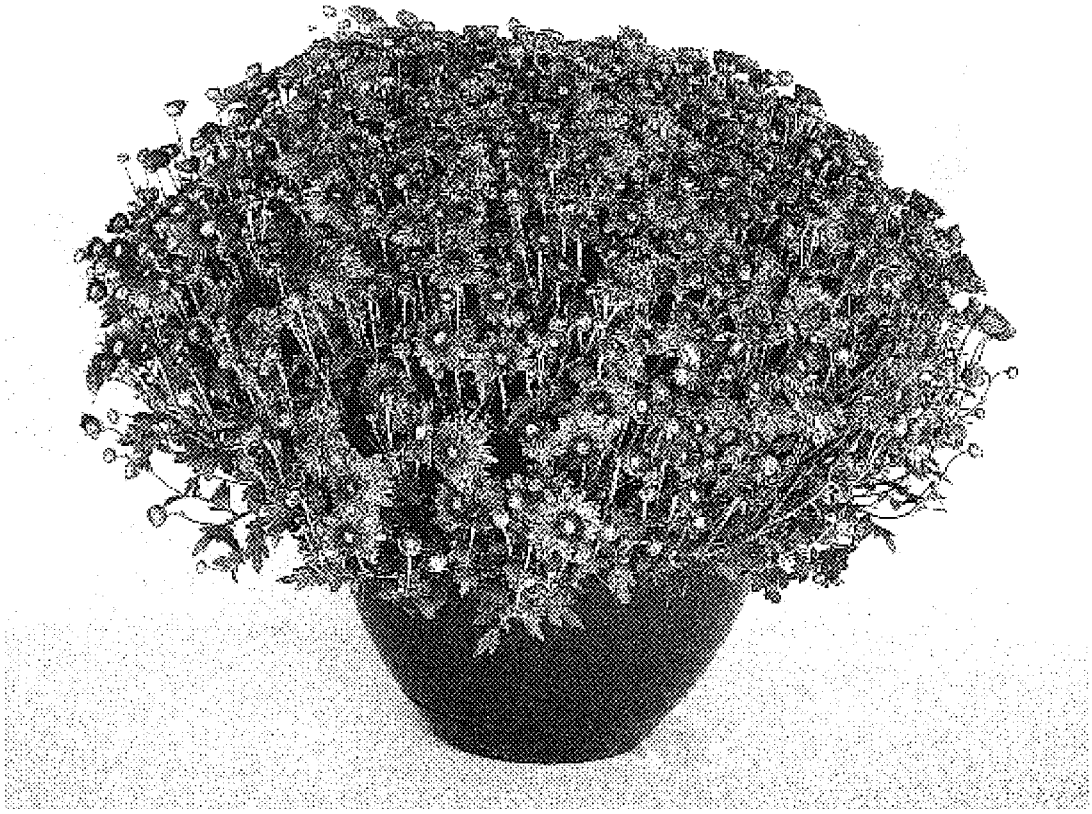

* * * * *